(12) United States Patent
Zhang et al.

(10) Patent No.: US 11,620,567 B2
(45) Date of Patent: Apr. 4, 2023

(54) METHOD, APPARATUS, DEVICE AND STORAGE MEDIUM FOR PREDICTING PROTEIN BINDING SITE

(71) Applicants: SHENZHEN UNIVERSITY, Guangdong (CN); HARBIN INSTITUTE OF TECHNOLOGY SHENZHEN GRADUATE SCHOOL, Guangdong (CN)

(72) Inventors: Yong Zhang, Guangdong (CN); Wei He, Guangdong (CN); Yong Xu, Guangdong (CN); Dongning Zhao, Guangdong (CN)

(73) Assignees: SHENZHEN UNIVERSITY, Shenzhen (CN); HARBIN INSTITUTE OF TECHNOLOGY SHENZHEN GRADUATE SCHOOL, Shenzhen (CN)

( * ) Notice: Subject to any disclaimer, the term of this patent is extended or adjusted under 35 U.S.C. 154(b) by 1107 days.

(21) Appl. No.: 16/255,857

(22) Filed: Jan. 24, 2019

(65) Prior Publication Data

US 2019/0156915 A1    May 23, 2019

Related U.S. Application Data

(63) Continuation of application No. PCT/CN2017/100314, filed on Sep. 4, 2017.

(30) Foreign Application Priority Data

Aug. 31, 2017  (CN) .......................... 201710770933.2

(51) Int. Cl.
*G16B 40/00* (2019.01)
*G06N 20/00* (2019.01)
(Continued)

(52) U.S. Cl.
CPC ............... *G06N 20/00* (2019.01); *G06N 5/04* (2013.01); *G16B 20/30* (2019.02); *G16B 30/00* (2019.02); *G16B 40/00* (2019.02)

(58) Field of Classification Search
CPC ........ G16B 30/00; G16B 20/00; G16B 30/10; G16B 40/00; G16B 20/30; G16B 40/20;
(Continued)

(56) References Cited

U.S. PATENT DOCUMENTS

2016/0148074 A1* 5/2016 Jean .................... G06F 16/5854
                                                                382/190

OTHER PUBLICATIONS

Zhou et al., PDNAsite: Identification of DNAbinding Site from Protein Sequence by Incorporating Spatial and Sequence Context, Jun. 10, 2016 [retrieved Aug. 22, 2022], Scientific Reports, vol. 6, Article No. 27653 (2016), pp. 1-15. Retrieved: https://www.nature.com/articles/srep27653 (Year: 2016).*

(Continued)

*Primary Examiner* — Matthew C Bella
*Assistant Examiner* — Dennis Rosario (57) ABSTRACT

The invention provides a method, apparatus, device and storage medium for predicting a protein binding site. The method comprises the steps of: receiving a protein sequence to be predicted, dividing the protein sequence by using a preset sliding window and sliding step to obtain a plurality of amino acid sub-sequences, building word vectors for the protein sequence according to the amino acid sub-sequences, extracting document features from word elements, building document feature vectors for the protein sequence according to the extracted document features, extracting protein chain biological features from the amino acid sub-sequences, building biological feature vectors for the protein sequence according to the extracted biological features, classifying the amino acid sub-sequences expressed with the document feature vectors and the biological feature vectors (Continued)

by using a preset amino acid residue classification model to obtain amino acid residue types for the protein sequence.

9 Claims, 3 Drawing Sheets (51) Int. Cl.
    *G06N 5/04*     (2023.01)
    *G16B 30/00*     (2019.01)
    *G16B 20/30*     (2019.01)

(58) Field of Classification Search
    CPC .............. G16B 40/30; G06T 7/0012; G06T 2207/30004; G06T 2207/20081; G06T 2207/20021; G06V 2201/03; G06V 20/698; G06N 3/08; G06N 20/00; G06K 9/6267; A61B 5/7267; A61B 5/7264
    See application file for complete search history.

(56) References Cited

OTHER PUBLICATIONS

Xu et al., Identification of DNA-binding proteins by incorporating evolutionary information into pseudo amino acid composition via the top-n-gram approach, Oct. 28, 2014 [retrieved Aug. 22, 2022], Journal of Biomolecular Structure and Dynamics, vol. 33, Issue 8, 13 pages. Retrieved: https://www.researchgate.net/publication/266152208_Identification_of_DNA-binding_proteins_by_incorporating_evolutionary_information_into_pseudo_amino_acid_composition_via_the_top-n-gram_approach (Year: 2014).*

Firdaus et al., Protein Structural Class Prediction Using Predicted Secondary Structure and Hydropathy Profile, Jul. 2013 [retrieved Aug. 22, 2022], C3S2E '13: Proceedings of the International C Conference on Computer Science and Software Engineering, pp. 49-57. Retrieved: https://dl.acm.org/doi/abs/10.1145/2494444.2494459 (Year: 2013).*

Lin et al., Classification and differential metabolite discovery of liver diseases based on plasma metabolic profiling and support vector machines, Sep. 15, 2011 [retrieved Aug. 22, 2022], Journal of Separation Science, vol. 34, Issue 21. pp. 3029-3036. Retrieved: https://analyticalsciencejournals.onlinelibrary.wiley.com/doi/full/10.1002/jssc.201100408 (Year: 2011).*

Cheng et al., Predicting RNA-binding sites of proteins using support vector machines and evolutionary information, Dec. 12, 2008 [retrieved Aug. 22, 2022], BMC Bioinformatics: Seventh International Conference on Bioinformatics, vol. 9, Supplement 12, 19 pages. (Year: 2005) Retrieved: https://bmcbioinformatics.biomedcentral.com/articles/10.1186/1471-2105-9-S12-S6 (Year: 2008).*

Dong et al., Application of latent semantic analysis to protein remote homology detection, Nov. 29, 2005 [retrieved Aug. 22, 2022], Bioinformatics, vol. 22, Issue 3, pp. 285-290. Retrieved: https://academic.oup.com/bioinformatics/article/22/3/285/220519 (Year: 2005).*

Wang et al., Prediction of Protein Secondary Structure using Support Vector Machine with PSSM Profiles, May 20-22, 2016 [retrieved Nov. 18, 2022], 2016 IEEE Information Technology, Networking, Elect and Auto Control Conf, pp. 502-505. Retrieved: https://ieeexplore.ieee.org/abstract/document/7560411 (Year: 2016).*

* cited by examiner

METHOD, APPARATUS, DEVICE AND STORAGE MEDIUM FOR PREDICTING PROTEIN BINDING SITE

CROSS REFERENCE TO RELATED APPLICATION

The present application is a Continuation Application of PCT application No. PCT/CN2017/100314 filed on Sep. 4, 2017, which claims the benefit of Chinese patent application No. 201710770933.2 filed on Aug. 31, 2017. All the above are hereby incorporated by reference.

BACKGROUND OF THE INVENTION

1. Technical Field

The invention belongs to the technical field of biological information, and in particular relates to a method, apparatus, device and storage medium for predicting a protein binding site.

2. Description of Related Art

In recent years, bioinformatics has received widespread attention from people, and more and more researchers in different fields have devoted themselves to the research work on the bioinformatics. As a comprehensive discipline that studies information content and information flow in the biology and biology related systems, the bioinformatics has a knowledge system incorporating the knowledge from many different disciplines, such as biology (genetics, biochemistry, etc.), mathematics (probability theory and mathematical statistics, algorithms, etc.), computer science (machine learning, computational theory, etc.), and physical chemistry (molecular modeling, thermodynamics, etc.).

As an embodiment of life activities and the most important basic unit by which all living beings express life, proteins can be regarded as the smallest automatic machine in nature, and have an irreplaceable role in the operation of biological systems. Different roles played by the proteins in cells are regulated by interactions between proteins, between proteins and DNAs, between proteins and RNAs, and between proteins and ligands. The protein-protein interactions involve the association of protein molecules, which plays a critical role in every biological process of living cells, such as DNA synthesis, gene transcriptional activation, protein translation, modification and localization, and information transmission. All of these important biological processes involve the protein-protein interactions. Thus, exploring the sequence and structural properties for the protein-protein interactions is of great importance for understanding cellular activities.

With the continuous development of the next-generation sequencing technology, the measured protein sequence data is increasing. As a result, there is a growing demand of people for computational tools that can quickly and reliably recognize protein binding sites. The localization of the protein binding sites is of great importance for the analysis and understanding of the molecular details of protein interactions and the protein functions. At present, the researches and predictions on the protein binding sites at home and abroad are mostly based on the physical and chemical features obtained by technically determining a single site, and the inter-site sequence features obtained by analyzing and calculating protein chains. This neglects the clustering property of the protein binding sites and the association information among amino acid residues, leading to low accuracy and generality in the prediction of the protein binding sites.

BRIEF SUMMARY OF THE INVENTION

An object of the invention is to provide a method, apparatus, computing device and storage medium for predicting a protein binding site, intended to solve the problems of low accuracy and generality in the prediction of the protein binding site in the prior art.

In one aspect, the invention provides a method for predicting a protein binding site, which comprises the following steps of:

receiving a protein sequence to be predicted, and dividing the protein sequence by using a preset sliding window and sliding step to obtain a plurality of amino acid sub-sequences forming the protein sequence;

building word vectors for the protein sequence according to the plurality of amino acid sub-sequences, with the word vectors having word elements to express the respective amino acid sub-sequences, extracting document features from the word elements, and building document feature vectors for the protein sequence according to the extracted document features;

extracting protein chain biological features from the amino acid sub-sequences expressed with the word elements, and building biological feature vectors for the protein sequence according to the extracted biological features; and classifying the document feature vectors and the biological feature vectors by using a preset amino acid residue classification model to obtain amino acid residue types for the protein sequence.

In another aspect, the invention provides an apparatus for predicting a protein binding site, which comprises:

a sequence division unit for receiving a protein sequence to be predicted, and dividing the protein sequence by using a preset sliding window and sliding step to obtain a plurality of amino acid sub-sequences forming the protein sequence;

a first vector building unit for building word vectors for the protein sequence according to the plurality of amino acid sub-sequences, with the word vectors having word elements to express the respective amino acid sub-sequences, extracting document features from the word elements, and building document feature vectors for the protein sequence according to the extracted document features;

a second vector building unit for extracting protein chain biological features from the amino acid sub-sequences expressed with the word elements, and building biological feature vectors for the protein sequence according to the extracted biological features; and a result acquisition unit for classifying the document feature vectors and the biological feature vectors by using a preset amino acid residue classification model to obtain amino acid residue types for the protein sequence.

In another aspect, the invention further provides a computing environment for dividing the sequence and building the classification model, as well as a computer program runnable in the environment, where the steps of the method for predicting the protein binding site as described are accomplished when the processor executes the computer program.

In another aspect, the invention further provides a computer-readable storage medium, which stores a computer program executed by a processor to accomplish the steps of the method for predicting the protein binding site as described.

The invention involves the steps of: receiving a protein sequence to be predicted, and dividing the protein sequence by using a preset sliding window and sliding step to obtain a plurality of amino acid sub-sequences forming the protein sequence to be predicted; building word vectors for the protein sequence according to the plurality of amino acid sub-sequences, with the word vectors having word elements to express the respective amino acid sub-sequences, extracting document features from word elements, and building document feature vectors for the protein sequence according to the extracted document features; extracting protein chain biological features from the amino acid sub-sequences, and building biological feature vectors for the protein sequence according to the extracted biological features; and classifying the amino acid sub-sequences expressed with both the document feature vectors and the biological feature vectors by using a preset amino acid residue classification model to obtain amino acid residue types for the protein sequence, thereby improving the accuracy and generality in the prediction of the protein binding site.

DETAILED DESCRIPTION OF THE INVENTION

To make the objects, technical solutions and advantages of the invention more clear and explicit, the invention will be further illustrated in detail with reference to the accompanying drawings and embodiments. It should be understood that the embodiments as described herein are only intended to explain, instead of limiting, the invention.

The specific implementation of the invention is described in detail below in conjunction with particular embodiments.

Embodiment 1

Figure 1:
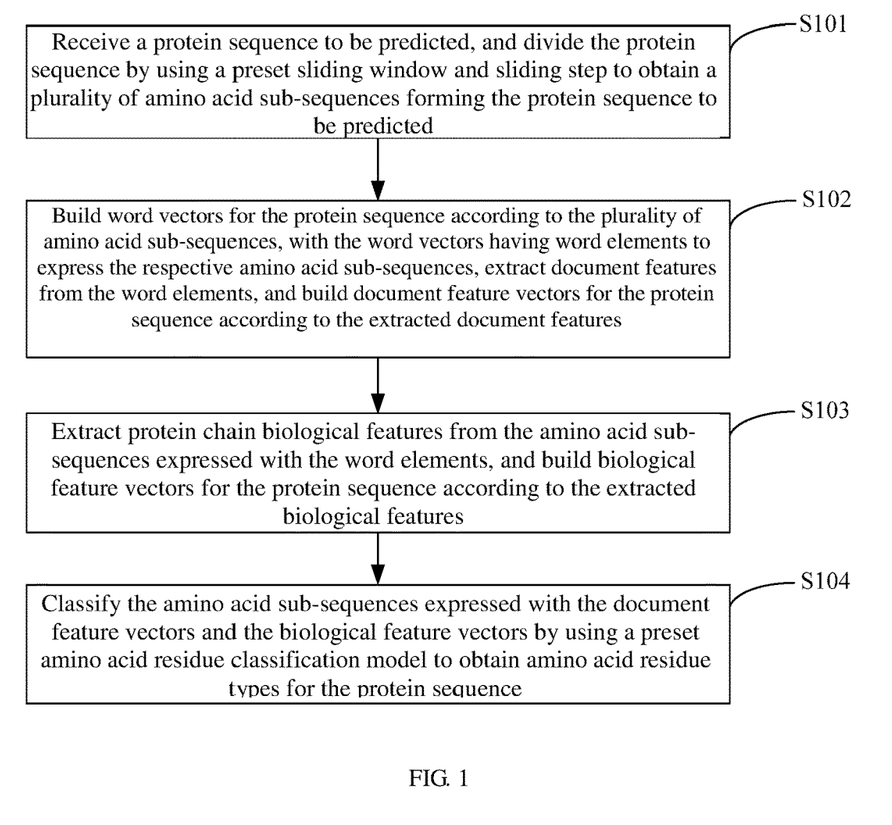
FIG. 1 is a flow chart showing the implementation of a method for predicting a protein binding site according to Embodiment 1 of the invention.

FIG. 1 shows a process flow for implementing a method for predicting a protein binding site provided by Embodiment 1 of the invention, which only shows sections related to the embodiment of the invention for the convenience of illustration, with the details described as follows.

At S101, receive a protein sequence to be predicted, and divide the protein sequence by using a preset sliding window and sliding step to obtain a plurality of amino acid sub-sequences forming the protein sequence to be predicted.

This embodiment of the invention is suitable for a system for predicting a protein binding site. In this embodiment of the invention, to embody the clustering property of a protein-protein binding site, the sliding window is started after the protein sequence to be predicted is received, the protein sequence is divided by adjusting the size of the sliding window and the sliding step to obtain a plurality of amino acid sub-sequences forming the protein sequence to be predicted, thereby taking local blocks of the protein sequence as subsequent analysis units.

In this embodiment of the invention, preferably, the sliding window has the size of (2*window+1−2*b), wherein window is a preset value, and b is a randomly generated variable ranging from 0 to window−1. This sliding window includes window−b neighborhood residues at each side of a target residue, and as the window slides on the amino acid sequence, its size randomly changes between 3(b=window−1) and 2*window+1(b=0) to obtain protein blocks formed by several amino acid residues, thereby facilitating subsequent analysis in which the protein blocks are taken as the basic units, which fully demonstrates the clustering property of the protein binding site and further improves the subsequent feature expression ability, prediction precision and generality.

Preferably, an amino acid residue classification model is obtained by training with machine learning before the protein sequence to be predicted is received. Preferably, a Stacking ensemble learning algorithm can be used for machine learning to improve the classification accuracy and generalization ability of the amino acid residue classification model.

Preferably, when the amino acid residue classification model is obtained by training with machine learning, a trained protein sequence in a preset training set is first divided by using a preset sliding window and sliding step to obtain a plurality of trained amino acid sub-sequences forming the trained protein sequence; then trained word vectors for the trained protein sequence are built according to the obtained plurality of trained amino acid sub-sequences, with the trained word vectors having trained word elements to express the respective trained amino acid sub-sequences, document features are extracted from the trained word elements, and trained document feature vectors are built for the trained protein sequence according to the extracted document features; protein chain biological features are extracted from the trained amino acid sub-sequences expressed with the trained word elements, and trained biological feature vectors are built for the trained protein sequence according to the extracted biological features; and finally, a pre-built classification model is trained by using the trained amino acid sub-sequences expressed with the trained document feature vectors and the trained biological feature vectors, and when a preset training termination condition is met, the classification model obtained from the training is set as the amino acid residue classification model. Therefore, the classification model is provided for the subsequent amino acid residue classification, which increases the classification efficiency of the classification model. Moreover, the training termination condition can be set as a preset number of times that the number of training times is to reach or a preset value that losses are to reach during training.

Specifically, a Stacking ensemble learning algorithm is used to train a preset model after many types of features are obtained, so as to obtain an amino acid residue classification model. At a first layer of the Stacking model, different types of protein chain biological features are used respectively to train multiple base classifiers, and then, prediction results of the multiple base classifiers are merged with the document feature vectors to serve as a final feature vector for training, thereby obtaining the amino acid residue classification model.

At S102, build word vectors for the protein sequence according to the plurality of amino acid sub-sequences, with the word vectors having word elements to express the respective amino acid sub-sequences, extract document features from the word elements, and build document feature vectors for the protein sequence according to the extracted document features.

In this embodiment of the invention, after a plurality of amino acid sub-sequences are obtained by dividing the sequence, word vectors are first built for the protein sequence according to the plurality of amino acid sub-sequences, with the word vectors having word elements to express the respective amino acid sub-sequences, document features are then extracted from the word elements, and finally, document feature vectors are built for the protein sequence according to the extracted document features. Moreover, the extracted document features include a TFIDF sequence feature and a N-gram sequence feature and others.

Preferably, when the word vectors are built for the protein sequence according to the amino acid sub-sequences, a unique number is allocated to every type of amino acid sub-sequence, and a word2vec algorithm is used to map the original unique numbers of the sub-sequences to a K-dimensional vector space to obtain the word vectors of the protein sequence. In this way, the feature dimension can be effectively reduced to seek feature expression at a deeper layer for the document data, and all the data in the high-dimensional word vectors are leveraged to make the data scale greater, which facilitates the subsequent classification effect.

At S103, extract protein chain biological features from the amino acid sub-sequences expressed with the word elements, and build biological feature vectors for the protein sequence according to the extracted biological features.

In this embodiment of the invention, the protein chain biological features are first extracted from the amino acid sub-sequences obtained by dividing the sequence, and then the biological feature vectors are built for the protein sequence according to the extracted biological features, where the extracted biological features include features such as a location specific scoring matrix feature and a pseudo amino acid composition feature, therefore, local information such as the order of appearance of the amino acid in the sequence is expressed effectively, enhancing the ability of the feature vectors for expressing the protein sequence information and further increasing the comprehensiveness of the biological features in the biological feature vectors.

At S104, classify the amino acid sub-sequences expressed with the document feature vectors and the biological feature vectors by using a preset amino acid residue classification model to obtain amino acid residue types for the protein sequence.

In this embodiment of the invention, the types of the amino acid residues are used to illustrate whether the amino acid residues are binding sites of the protein sequence. Preferably, when the document feature vectors and the biological feature vectors are classified, the biological feature vectors are first predicted, prediction results as predicted are then merged with the document feature vectors, and finally, the merged feature vectors obtained by feature merging are classified to further improve the accuracy in the prediction of the protein binding site. Moreover, the preset amino acid residue classification model is the amino acid residue classification model obtained through the foregoing training so that the accuracy in the prediction of the binding site of the protein sequence is improved.

Embodiment 2

Figure 2:
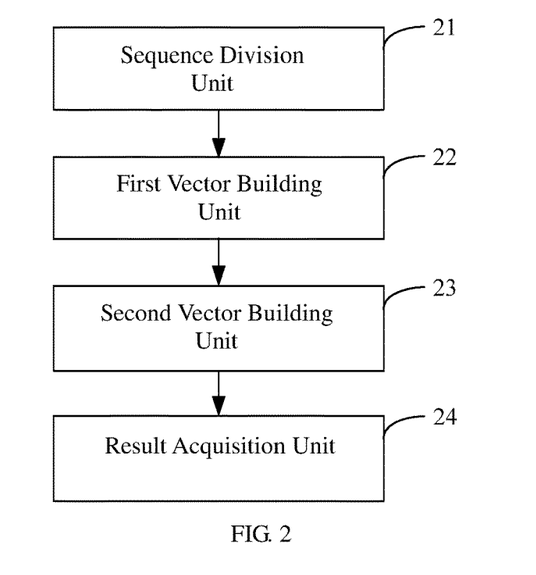
FIG. 2 is a schematic view showing the structure of an apparatus for predicting a protein binding site according to Embodiment 2 of the invention.

FIG. 2 shows a structure of an apparatus for predicting a protein binding site provided by Embodiment 2 of the invention, which only shows sections related to the embodiment of the invention for the convenience of illustration, wherein the apparatus comprises:

a sequence division unit 21 for receiving a protein sequence to be predicted, and dividing the protein sequence by using a preset sliding window and sliding step to obtain a plurality of amino acid sub-sequences forming the protein sequence to be predicted;

a first vector building unit 22 for building word vectors for the protein sequence according to the plurality of amino acid sub-sequences, with the word vectors having word elements to express the respective amino acid sub-sequences, extracting document features from the word elements, and building document feature vectors for the protein sequence according to the extracted document features;

a second vector building unit 23 for extracting protein chain biological features from the amino acid sub-sequences expressed with the word elements, and building biological feature vectors for the protein sequence according to the extracted biological features; and a result acquisition unit 24 for classifying the amino acid sub-sequences expressed with the document feature vectors and the biological feature vectors by using a preset amino acid residue classification model to obtain amino acid residue types for the protein sequence.

In this embodiment of the present, the sequence division unit 21 receives a protein sequence to be predicted, and divides the protein sequence by using a preset sliding window and sliding step to obtain a plurality of amino acid sub-sequences forming the protein sequence to be predicted; the first vector building unit 22 builds word vectors for the protein sequence according to the plurality of amino acid sub-sequences, with the word vectors having word elements to express the respective amino acid sub-sequences, extracts document features from word elements, and builds document feature vectors for the protein sequence according to the extracted document features; the second vector building unit 23 extracts protein chain biological features from the amino acid sub-sequences, and builds biological feature vectors for the protein sequence according to the extracted biological features; and the result acquisition unit 24 classifies the amino acid sub-sequences expressed with both the document feature vectors and the biological feature vectors by using a preset amino acid residue classification model to obtain amino acid residue types for the protein sequence, thereby improving the accuracy and generality in the prediction of the protein binding site.

In this embodiment of the invention, the respective units of the apparatus for predicting the protein binding site can be implemented with corresponding hardware or software units, and every unit may be either an independent software or hardware unit or an integrated software or hardware unit, which is not intended to limit the invention herein. The description of foregoing Embodiment 1 can be referred to for the particular implementations of respective units, which will not be repeated here.

Embodiment 3

Figure 3:
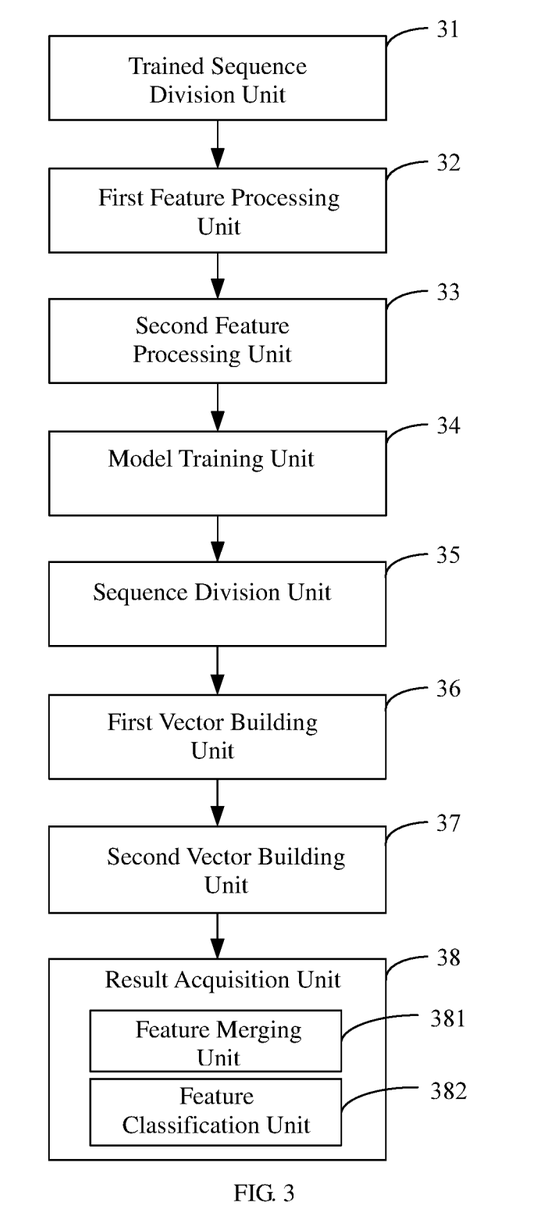
FIG. 3 is a schematic view showing the structure of an apparatus for predicting a protein binding site according to Embodiment 3 of the invention.

FIG. 3 shows a structure of an apparatus for predicting a protein binding site provided by Embodiment 3 of the invention, which only shows sections related to the embodiment of the invention for the convenience of illustration, wherein the apparatus comprises:

a trained sequence division unit 31 for dividing a trained protein sequence in a preset training set by using a preset sliding window and sliding step to obtain a plurality of trained amino acid sub-sequences forming the trained protein sequence;

a first feature processing unit 32 for building trained word vectors for the trained protein sequence according to the plurality of trained amino acid sub-sequences, with the trained word vectors having trained word elements to express the respective trained amino acid sub-sequences, extracting document features from the trained word elements, and building trained document feature vectors for the trained protein sequence according to the extracted document features;

a second feature processing unit 33 for extracting protein chain biological features from the trained amino acid sub-sequences expressed with the trained word elements, and building trained biological feature vectors for the trained protein sequence according to the extracted biological features; and a model training unit 34 for training a pre-built classification model by using the trained amino acid sub-sequences expressed with the trained document feature vectors and the trained biological feature vectors, and when a preset training termination condition is met, setting the classification model obtained from the training as the amino acid residue classification model.

In this embodiment of the invention, the amino acid residue classification model is obtained by training with machine learning before the protein sequence to be predicted is received. Preferably, a Stacking ensemble learning algorithm can be used for machine learning to improve the classification accuracy and generalization ability of the amino acid residue classification model.

Specifically, when the amino acid residue classification model is obtained by training with machine learning, the trained sequence division unit 31 first divides a trained protein sequence in a preset training set by using a preset sliding window and sliding step to obtain a plurality of trained amino acid sub-sequences forming the trained protein sequence; then the first feature processing unit 32 builds trained word vectors for the trained protein sequence according to the obtained plurality of trained amino acid sub-sequences, with the trained word vectors having trained word elements to express the respective trained amino acid sub-sequences, extracts document features from the trained word elements, and builds trained document feature vectors for the trained protein sequence according to the extracted document features; the second feature processing unit 33 extracts protein chain biological features from the trained amino acid sub-sequences expressed with the trained word elements, and builds trained biological feature vectors for the trained protein sequence according to the extracted biological features; and finally, the model training unit 34 trains a pre-built classification model by using the trained amino acid sub-sequences expressed with the trained document feature vectors and the trained biological feature vectors, and when a preset training termination condition is met, sets the classification model obtained from the training as the amino acid residue classification model. Therefore, the classification model is provided for the subsequent amino acid residue classification, which increases the classification efficiency of the classification model. Moreover, the training termination condition can be set as a preset number of times that the number of training times is to reach or a preset value that losses are to reach during training.

Specifically, a Stacking ensemble learning algorithm is used to train a preset model after many types of features are obtained, so as to obtain an amino acid residue classification model. At a first layer of the Stacking model, different types of protein chain biological features are used respectively to train multiple base classifiers, and then, prediction results of the multiple base classifiers are merged with the document feature vectors to serve as a final feature vector for training, thereby obtaining the amino acid residue classification model.

A sequence division unit 35 is used for receiving a protein sequence to be predicted, and dividing the protein sequence by using a preset sliding window and sliding step to obtain a plurality of amino acid sub-sequences forming the protein sequence to be predicted.

In this embodiment of the invention, to embody the clustering property of a protein-protein binding site, the sequence division unit 35 starts the sliding window after the protein sequence to be predicted is received, the protein sequence is divided by adjusting the size of the sliding window and the sliding step to obtain a plurality of amino acid sub-sequences forming the protein sequence to be predicted, thereby taking local blocks of the protein sequence as subsequent analysis units.

In this embodiment of the invention, preferably, the sliding window has the size of (2*window+1−2*b), wherein window is a preset value, and b is a randomly generated variable ranging from 0 to window−1. This sliding window includes window−b neighborhood residues at each side of a target residue, and as the window slides on the amino acid sequence, its size randomly changes between 3(b=window−1) and 2*window+1(b=0) to obtain protein blocks formed by several amino acid residues, facilitating subsequent analysis in which the protein blocks are taken as the basic units, which fully demonstrates the clustering property of the protein binding site and further improves the subsequent feature expression ability, prediction precision and generality.

A first vector building unit 36 is used for building word vectors for the protein sequence according to the plurality of amino acid sub-sequences, with the word vectors having word elements to express the respective amino acid sub-sequences, extracting document features from the word elements, and building document feature vectors for the protein sequence according to the extracted document features.

In this embodiment of the invention, after a plurality of amino acid sub-sequences are obtained by dividing the sequence, the first vector building unit 36 first builds word vectors for the protein sequence according to the plurality of amino acid sub-sequences, with the word vectors having word elements to express the respective amino acid sub-sequences, then extracts document features from the word elements, and finally builds document feature vectors for the protein sequence according to the extracted document features. Moreover, the extracted document features include a TFIDF sequence feature and an N-gram sequence feature and others.

Preferably, when the word vectors are built for the protein sequence according to the amino acid sub-sequences, a unique number is allocated to every type of amino acid sub-sequence, and a word2vec algorithm is used to map the original unique numbers of the sub-sequences to a K-dimensional vector space to obtain the word vectors of the protein sequence. In this way, the feature dimension can be effectively reduced to seek feature expression at a deeper layer for the document data, and all the data in the high-dimensional word vectors are leveraged to make the data scale greater, which facilitates the subsequent classification effect.

A second vector building unit 37 is used for extracting protein chain biological features from the amino acid sub-sequences expressed with the word elements, and building biological feature vectors for the protein sequence according to the extracted biological features.

In this embodiment of the invention, the second vector building unit 37 first extracts the protein chain biological features from the amino acid sub-sequences obtained by dividing the sequence, and then builds the biological feature vectors for the protein sequence according to the extracted biological features, where the extracted biological features include features such as a location specific scoring matrix feature and a pseudo amino acid composition feature, therefore, local information such as the order of appearance of the amino acid in the sequence is expressed effectively, enhancing the ability of the feature vectors for expressing the protein sequence information and further increasing the comprehensiveness of the biological features in the biological feature vectors.

A result acquisition unit 38 is used for classifying the amino acid sub-sequences expressed with the document feature vectors and the biological feature vectors by using a preset amino acid residue classification model to obtain amino acid residue types for the protein sequence.

In this embodiment of the invention, the types of the amino acid residues are used to illustrate whether the amino acid residues are binding sites of the protein sequence. Preferably, when the document feature vectors and the biological feature vectors are classified, the biological feature vectors are first predicted, prediction results as predicted are then merged with the document feature vectors, and finally, the merged feature vectors obtained by feature merging are classified to further improve the accuracy in the prediction of the protein binding site. Moreover, the preset amino acid residue classification model is the amino acid residue classification model obtained through the foregoing training so that the accuracy in the prediction of the binding site of the protein sequence is improved.

Therefore, preferably, the result acquisition unit 38 comprises:

a feature merging unit 381 for predicting the biological feature vectors and performing feature merging on prediction results predicted and the document feature vectors; and a feature classification unit 382 for classifying merged feature vectors obtained through the feature merging.

In this embodiment of the invention, the respective units of the apparatus for predicting the protein binding site can be implemented with corresponding hardware or software units, and every unit may be either an independent software or hardware unit or an integrated software or hardware unit, which is not intended to limit the invention herein.

Embodiment 4

Figure 4:
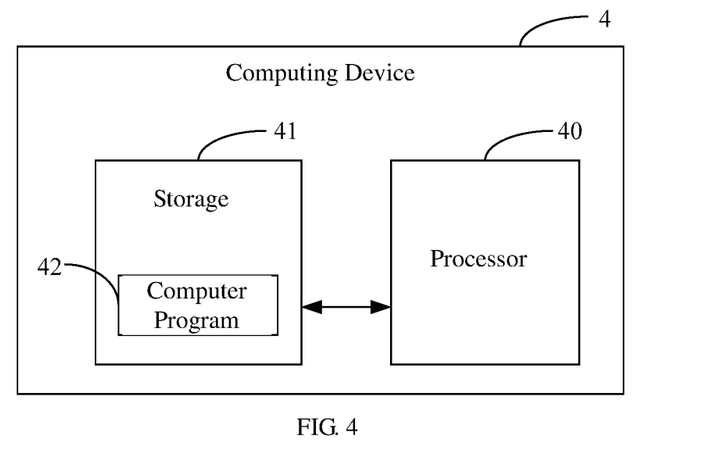
FIG. 4 is a schematic view showing the structure of a computing device provided by Embodiment 4 of the invention.

FIG. 4 shows a structure of a computing device provided in Embodiment 4 of the invention, which only shows sections related to the embodiment of the invention for the convenience of illustration.

The computing device 4 in the embodiment of the invention comprises a processor 40, a storage 41 and a computer program 42 stored in the storage 41 and runnable on the processor 40. The processor 40 executes the computer program 42 to accomplish the steps in the embodiment of the method for predicting the protein binding site as described above, for example, S101 to S104 shown in FIG. 1. Or, the processor 40 executes the computer program 42 to accomplish the functions of respective units in the embodiments of each apparatus above, for example, the functions of the units 21 to 24 shown in FIG. 2 and the units 31 to 38 shown in FIG. 3.

In this embodiment of the invention, when the processor 40 executes the computer program 42 to accomplish the steps in the embodiment of the method for predicting the respective protein binding site above, a protein sequence to be predicted is received divided by using a preset sliding window and sliding step to obtain a plurality of amino acid sub-sequences forming the protein sequence to be predicted; word vectors are built for the protein sequence according to the plurality of amino acid sub-sequences, with the word vectors having word elements expressing the respective amino acid sub-sequences, document features are extracted from word elements, and document feature vectors are built for the protein sequence according to the extracted document features; protein chain biological features are extracted from the amino acid sub-sequences, and biological feature vectors are built for the protein sequence according to the extracted biological features; and the amino acid sub-sequences expressed with both the document feature vectors and the biological feature vectors are classified by using a preset amino acid residue classification model to obtain amino acid residue types for the protein sequence, thereby improving the accuracy and generality in the prediction of the protein binding site. The method described in this Embodiment can be referred to Embodiment 1 for the details of the steps accomplished when the processor 40 in the computing device 4 executes the computer program, which will not be repeated here.

Embodiment 5

In this embodiment of the invention, a computer-readable storage medium is provided, which stores a computer program executed by a processor to accomplish the steps in the embodiment of the method for predicting the protein binding site above, for example, S101 to S104 shown in FIG. 1. Or, the computer program is executed by the processor to accomplish the functions of respective units in the embodiments of each apparatus above, for example, the functions of the units 21 to 24 shown in FIG. 2 and the units 31 to 38 shown in FIG. 3.

This embodiment of the invention involves the steps of: receiving a protein sequence to be predicted, and dividing the protein sequence by using a preset sliding window and sliding step to obtain a plurality of amino acid sub-sequences forming the protein sequence to be predicted; building word vectors for the protein sequence according to the plurality of amino acid sub-sequences, with the word vectors having word elements to express the respective amino acid sub-sequences, extracting document features from word elements, and building document feature vectors for the protein sequence according to the extracted document features; extracting protein chain biological features from the amino acid sub-sequences expressed with the word elements, and building biological feature vectors for the protein sequence according to the extracted biological features; and classifying the amino acid sub-sequences expressed with the document feature vectors and the biological feature vectors by using a preset amino acid residue classification model to obtain amino acid residue types for the protein sequence, thereby improving the accuracy and generality in the prediction of the protein binding site. The steps described in the embodiment of the method can be further referred to for the method for predicting the protein binding site as accomplished when the computer program is executed by the processor, which will not be repeated here.

The computer readable storage medium of the embodiment of the invention may include any entity or apparatus capable of carrying computer program codes and recording medium, for example, storages such as ROM/RAM, disks, optical disks and flash memories.

The description above provides only preferred embodiments of the invention, but is not intended to limit the invention. Any modifications, equivalent substitutions, improvements and the like made within the spirit and principle of the invention are construed to be incorporated within the protection scope of the invention.

What is claimed is:

1. A method for predicting a protein binding site, comprising the following steps of:
   receiving a protein sequence to be predicted, and dividing the protein sequence by using a preset sliding window and sliding step to obtain a plurality of amino acid sub-sequences forming the protein sequence;
   building word vectors for the protein sequence according to the plurality of amino acid sub-sequences, with the word vectors having word elements to express the respective amino acid sub-sequences, extracting document features from the word elements, and building document feature vectors for the protein sequence according to the extracted document features;
   extracting protein chain biological features from the amino acid sub-sequences expressed with the word elements, and building biological feature vectors for the protein sequence according to the extracted protein chain biological features; and
   classifying the amino acid sub-sequences expressed with the document feature vectors and the biological feature vectors by using a preset amino acid residue classification model to obtain amino acid residue types for the protein sequence;
   wherein the preset sliding window has the size of (2*window+1−2*b), the window is a preset value, and b is a randomly generated variable ranging from 0 to window−1.

2. The method according to claim 1, wherein before the step of receiving a protein sequence to be predicted, the method further comprises the steps of:
   dividing a trained protein sequence in a preset training set by using a preset sliding window and sliding step to obtain a plurality of trained amino acid sub-sequences forming the trained protein sequence;
   building trained word vectors for the trained protein sequence according to the plurality of amino acid sub-sequences, with the trained word vectors having trained word elements to express the respective trained amino acid sub-sequences, extracting document features from the trained word elements, and building trained document feature vectors for the trained protein sequence according to the extracted document features;
   extracting protein chain biological features from the trained amino acid sub-sequences expressed with the trained word elements, and building trained biological feature vectors for the trained protein sequence according to the extracted protein chain biological features; and
   training a pre-built classification model by using the trained amino acid sub-sequences expressed with the trained document feature vectors and the trained biological feature vectors, and when a preset training termination condition is met, setting the pre-built classification model obtained from the training as the amino acid residue classification model.

3. The method according to claim 2, wherein the document features comprise a Term Frequency-Invers Document Frequency (TFIDF) sequence feature and a N-gram sequence feature, and the protein chain biological features comprise a location specific scoring matrix feature and a pseudo amino acid composition feature.

4. The method according to claim 1, wherein the document features comprise a Term Frequency-Invers Document Frequency (TFIDF) sequence feature and a N-gram sequence feature, and the protein chain biological features comprise a location specific scoring matrix feature and a pseudo amino acid composition feature.

5. The method according to claim 1, wherein the step of classifying the document feature vectors and the biological feature vectors by using a preset amino acid residue classification model comprises the sub-steps of:
   predicting the biological feature vectors and performing feature merging on prediction results predicted and the document feature vectors; and
   classifying merged feature vectors obtained through the feature merging.

6. An apparatus for predicting a protein binding site, comprising:
   a sequence division unit for receiving a protein sequence to be predicted, and dividing the protein sequence by using a preset sliding window and sliding step to obtain a plurality of amino acid sub-sequences forming the protein sequence;
   a first vector building unit for building word vectors for the protein sequence according to the plurality of amino acid sub-sequences, with the word vectors having word elements to express the respective amino acid sub-sequences, extracting document features from the word elements, and building document feature vectors for the protein sequence according to the extracted document features;
   a second vector building unit for extracting protein chain biological features from the amino acid sub-sequences expressed with the word elements, and building biological feature vectors for the protein sequence according to the extracted protein chain biological features; and
   a result acquisition unit for classifying the amino acid sub-sequences expressed with the document feature vectors and the biological feature vectors by using a preset amino acid residue classification model to obtain amino acid residue types for the protein sequence;
   wherein the preset sliding window has the size of (2*window+1−2*b), the window is a preset value, and b is a randomly generated variable ranging from 0 to window−1.

7. The apparatus according to claim 6, further comprising:
   a trained sequence division unit for dividing a trained protein sequence in a preset training set by using a preset sliding window and sliding step to obtain a plurality of trained amino acid sub-sequences forming the trained protein sequence;
   a first feature processing unit for building trained word vectors for the trained protein sequence according to the plurality of amino acid sub-sequences, with the trained word vectors having trained word elements to express the respective trained amino acid sub-sequences, extracting document features from the trained word elements, and building trained document feature vectors for the trained protein sequence according to the extracted document features;

a second feature processing unit for extracting protein chain biological features from the trained amino acid sub-sequences expressed with the trained word elements, and building trained biological feature vectors for the trained protein sequence according to the extracted protein chain biological features; and a model training unit for training a pre-built classification model by using the trained amino acid sub-sequences expressed with the trained document feature vectors and the trained biological feature vectors, and when a preset training termination condition is met, setting the pre-built classification model obtained from the training as the amino acid residue classification model.

8. The apparatus according to claim 6, wherein the result acquisition unit comprises:

a feature merging unit for predicting the biological feature vectors and performing feature merging on prediction results predicted and the document feature vectors; and a feature classification unit for classifying merged feature vectors obtained through the feature merging.

9. A computing device, comprising a storage, a processor and a computer program stored in the storage and runnable on the processor, wherein the processor executes the computer program to accomplish the steps of the method of claim 1.

* * * * *